(12) United States Patent
Negi et al.

(10) Patent No.: US 7,053,218 B2
(45) Date of Patent: May 30, 2006

(54) **PROCESS FOR REGIOSELECTIVE DEMETHYLATION OF *P*-METHOXY GROUP IN PHENOLIC ESTER AND DIARYL KETONE MOIETIES**

(75) Inventors: Arvind Singh Negi, Lucknow (IN); Sunil Kumar Chattopadhyay, Lucknow (IN); Sachin Srivastava, Lucknow (IN); Asish Kumar Bhattacharya, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 21 days.

(21) Appl. No.: 10/937,096

(22) Filed: Sep. 8, 2004

(65) Prior Publication Data

US 2006/0052463 A1    Mar. 9, 2006

(51) Int. Cl.
 *C07D 471/00* (2006.01)
 *C07C 69/76* (2006.01)
 *C07C 45/00* (2006.01)
 *C07C 39/00* (2006.01)

(52) U.S. Cl. .............................. 546/53; 560/8; 560/55; 568/312; 568/315; 568/715; 568/716

(58) Field of Classification Search .................... 560/8, 560/55; 568/312, 315, 715, 716; 546/53
See application file for complete search history.

(56) References Cited

U.S. PATENT DOCUMENTS 4,191,841 A * 3/1980 Soreau et al. ................ 562/475

OTHER PUBLICATIONS

Dodge et al, Regeoselectivity in the Alkaline Thiolate Deprotection of Aryl Methyl Ethers, Journal of Organic Chemostry 60 (3), 739-741, 1995.*

* cited by examiner

*Primary Examiner*—J. Parsa
(74) *Attorney, Agent, or Firm*—TraskBritt

(57) ABSTRACT

Demethylation of 3', 4'-dimethoxy or 3', 4', 5'-trimethoxy benzoic ester of a phenol is carried out in the presence of an excess of aluminum halide in an organic solvent to get 4'-Hydroxy, 3'-methoxy or 4' hydroxy, 3', 5'-dimethoxy benzoic acid ester of a phenol. The reaction is also applicable to 3', 4', 5'-trimethoxy diaryl ketone and some natural products like reserpine.

7 Claims, No Drawings

PROCESS FOR REGIOSELECTIVE DEMETHYLATION OF P-METHOXY GROUP IN PHENOLIC ESTER AND DIARYL KETONE MOIETIES

TECHNICAL FIELD

The present invention relates to a process for manufacturing 4'-hydroxy-3'-methoxy benzoic acid ester of a phenol from 3',4'-dimethoxy benzoic acid ester of a phenol and 4'-hydroxy-3',5'-dimethoxy benzoic acid ester of a phenol from 3', 4', 5'-trimethoxy benzoic acid ester of a phenol. The process is also applicable for manufacturing 4'-hydroxy, 3', 5'-dimethoxy naphthophenone derivatives from 3', 4', 5'-trimethoxy naphthophenone derivatives.

All products have been confirmed by $^1$HNMR, $^{13}$CNMR and by literature data of these compounds.

Scheme 1

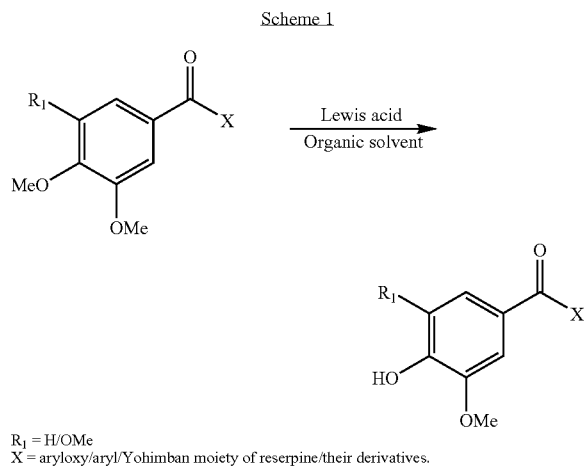

$R_1$ = H/OMe
X = aryloxy/aryl/Yohimban moiety of reserpine/their derivatives.

BACKGROUND

Demethylation of phenolic ethers is done by a number of methods. Usually boron tri bromide ($BBr_3$), pyridinium chloride (pyridine-HCl), Lithium aluminum hydride (LAH), aluminum chloride ($AlCl_3$) as such or with a variety of solvents like petroleum ether, ethyl acetate-HCl, EtSH, L-Selectride (Lithium tri-sec-butyl Hydride), etc., have been used as demethylating agents in the synthesis of different compounds.

The most common reagent for demethylation of phenolic ethers is pyridinium chloride, which provides no regioselectivity. Ijaz et al. (*Ind. J. Chem.*, Sec. B (1994), 33B(3), 288–289), have used pyridinium hydrobromideperbromide for the demethylation of arylmethyl ethers, but there was no regioselectivity in this method. Hwang et al. (*Synthetic Comm.* (1993), 23(20), 2845–2849), have reported demethylation of p-alkoxy-phenyl methyl ethers with 48% hydrobromic acid in presence of tetrabutyl phosphorus bromide ($BU_4PBr$). Bastow et al. (*Bioorg. Med. Chem.* (1993), 1(3), 227–234), have demethylated all the four methoxy ethers of colchicine by using 1M $BBr_3$ in dicholoromethane. Among the selective demethylation methods Lal et al. (*J. Org. Chem.* (1987), 52(6), 1072–1078), have used sodium thioxide ($C_2H_5SNa$) in DMF for the demethylation of orthomethoxy groups in some aromatic alcohols bearing 2,4-dimethoxy and 2, 3, 4-trimethoxy derivatives. Horie et al. (*J. Org. Chem.* (1987), 52(21), 4702–4709), selectively demethylated 7-hydroxy-3, 5, 8-trimethoxy flavones with aluminum bromide in acetonitrile to 5,7-dihydroxy and 3,7-dihydroxy flavone derivatives. Another demethylation approach was developed by Horie et al. (*Chem. Pharm. Bull.* (1987), 35(11), 4465–4472), in which they have selectively demethylated ortho-methoxy group in 2, 3, 4, 6-tetra methoxy acetophenone-type moieties by aluminum bromide in acetonitrile. Demettenaere et al. (*Tetrahedron* (2002), 58, 2163), have reported a similar method in which they have demethylated both the 2,4-dimethoxy groups in a 2, 4, 5-trimethoxy benzaldehyde by using aluminum chloride.

A similar method for regioselective demethylation of 3, 4, 5-trimethoxy benzoic acid has been done by Soreau et al. (U.S. Pat. No. 4,191,841) to 4-hydroxy-3,5-dimethoxy benzoic acid by using an excess of alkali hydroxide in an amount of ethylene glycol.

So far, there is no such report on regioselective demethylation of p-methoxy group in a 3,4-dimethoxy and/or 3, 4, 5-trimethoxy derivatives of benzoic acid esters and diaryl ketone derivatives.

SUMMARY OF THE INVENTION

This invention provides a novel process for regioselective demethylation of 3', 4', 5'-trimethoxy benzoic acid ester of a phenol/3', 4', 5'-trimethoxy diaryl ketone moiety using a lewis acid and organic solvent. The process is also applicable to some natural products also. A simple, economical, selective and high-yielding procedure for: the rapid demethylation of p-methyl ethers has been developed using reagents and solvents suitable for production of medicinal products. This procedure is superior to other demethylation methodologies. The method should prove generally useful for the rapid demethylation of p-hydroxy aryl methyl ethers. The reaction will be very useful in synthesizing analogs of some natural products.

An object of this invention is to provide a regioselective method for demethylation of phenolic ethers, such as, 3',4'-dimethoxy, 3', 4', 5'-trimethoxy benzoic acid esters and 3', 4', 5'-trimethoxy diaryl ketones.

Further, the object of this invention is to apply this method in some natural products having the minimal requisite structure, such as, reserpine to synthesize 4'-O-desmethyl reserpine.

A further object of the invention is to provide a demethylation method which will be suitable for the production of pharmaceutical products intended for human use.

Another object of this invention is to develop a method for selective demethylation of phenolic ethers, which will help in Quantitative Structure and Activity Relationship (QSAR) studies.

Further, another object of this invention is to provide a demethylation method that will give different analogs for biological activity.

DETAILED DESCRIPTION OF THE INVENTION

Accordingly, the present invention provides a process for regioselective demethylation of a compound of general formula 1

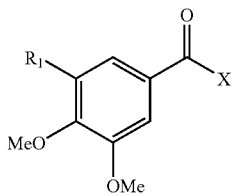

Formula 1

Wherein,
R₁=H/OMe
X=aryloxy/aryl/Yohimban moiety of reserpine/their derivatives.

to obtain a compound of general formula 2,

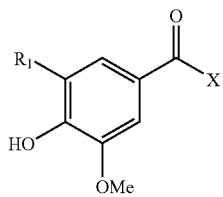

Formula 2

Wherein,
R₁=H/OMe
X=aryloxy/aryl/Yohimban moiety of reserpine/their derivatives.

said process comprises steps:
(a) mixing compound of formula 1 with an organic solvent;
(b) adding Lewis acid to mixture of step (a) and stirring the reaction mixture at a temperature in the range of 0–80° C. for a time period in the range of 5 minutes to 3 hours; and
(c) adding mineral acid into the reaction mixture of step (b), further stirring the mixture for a time period in the range of 2–10 minutes to obtain a demethylated compound of general formula 2.

In another embodiment of the invention, the organic solvent in step (a) is selected from a group comprising dry Chloroform, Dichloromethane, Acetonitrile and Dimethylformamide.

In yet another embodiment of the invention, the preferred organic solvent is Dichloromethane.

In another embodiment of the invention, the Lewis acid in step (b) is selected from a group comprising Aluminum chloride, Aluminum bromide, Tribromoborane, Stannous chloride.

In a further embodiment, the preferred Lewis acid is Aluminum chloride.

In another embodiment of the invention, in step (c) mineral acid is selected from a group comprising sulfuric acid and hydrochloric acid.

In another embodiment of the invention, formula 1 is selected from a group comprising p-methyl ethers, 3', 4', 5'-trimethoxydiaryl ketone and few natural products like reserpine and their derivatives.

The present invention provides a method for manufacturing p-demethylated derivatives of 3',4'-dimethoxy/3', 4', 5'-trimethoxy carboxylic acid esters of phenols and 3', 4', 5'-trimethoxy diaryl ketones. For all the type of substrates the reaction conditions are same.

The substrate is dissolved in a solvent. An excess amount of Lewis acid is added to it and reaction mixture is further stirred at room temperature. The reaction is applicable to the substrates wherein;
a. The substrate may be phenolic esters of 3,4-dimethoxy benzoic acid, wherein the phenolic group may be from a group of phenolic compounds like phenol, 1-naphthol, 2-naphthol, etc.
b. The substrate may be phenolic esters of 3, 4, 5-trimethoxy benzoic acid, wherein the phenolic compound may be from a group of phenolic compounds like phenol, 1-naphthol, 2-naphthol, etc.
c. The substrate may be diaryl ketones with 3, 4, 5-trimethoxy ether groups, wherein the aryl groups may be from a group of compounds having an aromatic ring, such as phenyl, 1-naphthyl, 2-naphthyl, etc.
d. The solvent used in this process may be from a group of organic solvents like $CHCl_3$, $CH_2Cl_2$, $CH_3CN$, DMF, etc.
e. The catalyst used in the process may be from a group of Lewis acids like $AlCl_3$, $AlBr_3$, $BBr_3$, $SnCl_4$, etc., and mineral acids like $H_2SO_4$, HCl, etc.
f. The temperature in the process may be in the range 0–80° C.

In order that the invention may be more fully understood, some preferred embodiments of practicing the method according to the invention are described below, purely by way of illustrative, but non-limiting, examples.

General method for preparation of Aryl 4'-Hydroxy, 3'-methoxy benzoate, Aryl 4'-hydroxy and Aryl 4'-hydroxy, 3',5'-dimethoxy benzoate, 4'-hydroxy, 3',5'-dimethoxy diaryl ketone or their derivatives:

Syntheses of 2-naphthyl, 4'-hydroxy, 3'-methoxy benzoate from 2-naphthyl-3', 4'-dimethoxy benzoate/phenyl 4'-hydroxy, 3',5'-dimethoxy benzoate from phenyl-3', 4', 5'-trimethoxy benzoate/1-naphthyl, 4'-hydroxy, 3',5'-dimethoxy benzoate from 1-naphthyl, 3', 4', 5'-trimethoxy benzoate/2-naphthyl, 4'-hydroxy, 3',5'-dimethoxy benzoate from 2-naphthyl, 3', 4', 5'-trimethoxy benzoate/2,4'-dihydroxy, 3,5-dimethoxy naphthophenone from 2-hydroxy, 3', 4', 5'-trimethoxy naphthophenone/4'-hydroxy, 3,5-dimethoxy naphthophenone, 2-O-acetic acid from 3', 4', 5'-trimethoxy naphthophenone, 2-O-acetic acid.

EXAMPLE 1

Synthesis of 2-naphthyl, 4'-hydroxy, 3',5'-dimethoxy benzoate from 2-naphthyl, 3', 4', 5'-trimethoxy benzoate In a 25 ml r.b. flask 100 mg of 2-naphthyl, 3', 4', 5'-trimethoxy benzoate was taken in 10 ml dry dichloromethane. Now, 1.0 g anhydrous aluminum chloride was added to it. The reaction mixture was further stirred at room temperature (25° C.). After 30 minutes when the reacton is complete, 5% dil.HCl was added to the reaction mixture and stirred for 5 minutes. The reaction mixture was washed with water and the organic layer dried over anhydrous sodium sulphate. The organic layer was distilled off to get an oil which was chromatographed through silica gel column to get the demethylated compound, i.e., 2-naphthyl, 4'-hydroxy, 3', 5'-dimethoxy benzoate. It was recrystallized with hexane-Chloroform (Yield: 71.6 mg, 74.6%).

Preparation of 4'-O-desmethyl reserpine from reserpine

In a 25 ml r.b. flask, 100 mg of reserpine was taken in 10 ml dry dichloromethane. To this stirring reaction mixture, 1 g anhydrous aluminum chloride was added and further stirred for 2 hours. After the completion of reaction, 10 ml 5% HCl was added to it and stirred for 5 minutes. It was extracted with chloroform and washed with water. The organic layer was dried over anhydrous sodium sulphate and was distilled off. The crude oil thus obtained was purified through a preparative TLC plate. To get pure O-desmethyl Reserpine (Yield: 46 mg, 47.1%).

EXAMPLE 2

Synthesis of 2-naphthyl, 4'-hydroxy, 3',5'-dimethoxy benzoate from 2-naphthyl, 3', 4, 5'-trimethoxy benzoate In a 25 ml r.b. flask, 100 mg of 2-naphthyl, 3', 4', 5'-trimethoxy benzoate was taken in 10 ml dry acetonitrile. Now 1.0 g anhydrous aluminum chloride was added to it. The reaction mixture was further stirred at 25° C. After 50 minutes when the reaction is complete, 5% dil.HCl was added to the reaction mixture and stirred for 5 minutes. The reaction mixture was washed with water and the organic layer dried over anhydrous sodium sulphate. The organic layer was distilled off to get oil. It was recrystallized to get pure 2-naphthyl, 4'-hydroxy, 3', 5'-dimethoxy benzoate (Yield: 32.6 mg, 34%).

Preparation of 4'-O-desmethyl reserpine from reserpine

In a 25 ml r.b. flask, 100 mg of reserpine was taken in 10 ml dry acetonitrile. To this stirring reaction mixture, 1 g anhydrous aluminum chloride was added and further stirred for 2 hours at 25° C. After the completion of reaction, 10 ml 5% HCl was added to it and stirred for 5 minutes. It was extracted with chloroform and washed with water. The organic layer was dried over anhydrous sodium sulphate and was distilled off. The crude oil thus obtained was purified through. It was passed through a small silica column or a preparative TLC plate to get pure 4'-O-desmethyl Reserpine (Yield: 21.9 mg, 22.4%).

EXAMPLE 3

Synthesis of 2-naphthyl, 4'-hydroxy, 3',5'-dimethoxy benzoate from 2-naphthyl, 3', 4', 5'-trimethoxy benzoate In a 25 ml r.b. flask. 100 mg of 2-naphthyl, 3', 4', 5'-trimethoxy benzoate was taken in 10 ml dry dichloromethane. Now, 500 mg to 1.0 g anhydrous aluminum bromide was added to it. The reaction mixture was further stirred at 25° C. After 50 minutes when the reaction is complete, 5% dil.HCl was added to the reaction mixture and stirred for 5 minutes. The reaction mixture was washed with water and the organic layer dried over anhydrous sodium sulphate. The organic layer was distilled off to get oil. It was column chromatographed over silica gel to get pure 2-naphthyl, 4'-hydroxy, 3',5'-dimethoxy benzoate (Yield: 32.6 mg, 34%).

Preparation of 4'-O-desmethyl reserpine from reserpine

In a 25 ml r.b. flask, 100 mg of reserpine was taken in 10 ml dry dichloromethane. To this stirring reaction mixture, 1 g anhydrous aluminum bromide was added and further stirred for 2 hours at 25° C. After the completion of reaction, 10 ml 5% HCl was added to it and stirred for 5 minutes. It was extracted with chloroform and washed with water. The organic layer was dried over anhydrous sodium sulphate was distilled off. The crude oil thus obtained was purified through. It was passed through a small silica column or a preparative TLC plate to get pure O-desmethyl reserpine (Yield: 21.9 mg 22.4%).

Advantages:

1. The process is novel as there is no such report on regioselective demethylation of diaryl ketones and phenolic esters at the p-position.

2. The process is highly regioselective and applicable to all compounds having the chemical structure as depicted in Schemes 1.

3. The process may be used in pharmaceutical products as the chemicals and solvents used are not toxic in nature.

4. All the reagents and solvents used are readily available and very cheap so the process is commercially viable.

5. The reaction is straight forward and, in most of the cases, the reaction goes completely.

6. The process is very simple, economic and does not require harsh reaction conditions.

What is claimed is:

1. A process for regioselective demethylation of a compound of general formula 1

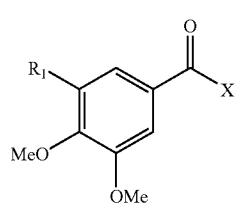

Formula 1

Wherein,
R_1=H/OMe
X=aryloxy/aryl/Yohimban moiety of reserpine/their derivatives.

to obtain a compound of general formula 2,

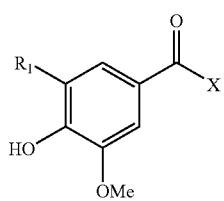

Formula 2

Wherein,
R_1=H/OMe
X=aryloxy/aryl/Yohimban moiety of reserpine/their derivatives.

said process comprises steps:
 (a) mixing compound of formula 1 with an organic solvent;
 (b) adding Lewis acid to mixture of step (a) and stirring the reaction mixture at a temperature in the range of 0 to 80° C. for a time period in the range of 5 minutes to 3 hours; and
 (c) adding mineral acid into the reaction mixture of step (b), further stirring the mixture for a time period in the range of 2 to 10 minutes to obtain a demethylated compound of general formula 2.

2. The process as claimed in claim 1, wherein the organic solvent in step (a) is selected from a group consisting of dry Chloroform, Dichloromethane, Acetonitrile and Dimethylformamide.

3. The process as claimed in claim 2, wherein the organic solvent is Dichloromethane.

4. The process as claimed in claim 1, wherein the Lewis acid in step (b) is selected from a group consisting of Aluminum chloride, Aluminum bromide, Tribromoborane, and Stannous chloride.

5. The process as claimed in claim 3, wherein the preferred Lewis acid is Aluminum chloride.

6. The process as claimed in claim 1, wherein in step (c) mineral acid is selected from a group consisting of sulfuric acid and hydrochloric acid.

7. The process as claimed in claim 1, wherein formula 1 is selected from a group consisting of p-methyl ethers, 3', 4', 5'-trimethoxydiaryl ketone, reserpine and their derivatives.

* * * * *

UNITED STATES PATENT AND TRADEMARK OFFICE
CERTIFICATE OF CORRECTION

PATENT NO. : 7,053,218 B2  
APPLICATION NO. : 10/937096  
DATED : May 30, 2006  
INVENTOR(S) : Arvind Singh Negi et al.

It is certified that error appears in the above-identified patent and that said Letters Patent is hereby corrected as shown below:

On the title page:
In item (56) titled References Cited OTHER PUBLICATIONS,
1st line, change "Regeoselectivity" to --Regioselectivity--

3rd line, change "Chemostry" to --Chemistry--

In the specification:

| | | |
|---|---|---|
| COLUMN 1, | LINE 61, | change "dicholoromethane." to --dichloromethane.-- |
| COLUMN 2, | LINE 30, | change "lewis acid" to --Lewis acid-- |
| COLUMN 5, | LINE 13, | change "TLC Plate. To get" to --TLC Plate to get-- |
| COLUMN 5, | LINE 56, | change "r.b. flask. 100 mg" to --r.b. flask, 100 mg-- |
| COLUMN 6, | LINE 10, | change "sulphate was" to --sulphate and was-- |

Signed and Sealed this

Twenty-fifth Day of March, 2008

JON W. DUDAS  
*Director of the United States Patent and Trademark Office*